United States Patent [19]

Nettleton, Jr. et al.

[11] 4,064,014
[45] Dec. 20, 1977

[54] ANTIBIOTIC COMPOUNDS MARCELLOMYCIN AND MUSETTAMYCIN

[75] Inventors: Donald E. Nettleton, Jr., Jordan; James A. Bush, Fayetteville; William T. Bradner, Manlius; Richard H. Schreiber, Canastota, all of N.Y.

[73] Assignee: Bristol-Myers Company, New York, N.Y.

[21] Appl. No.: 780,561

[22] Filed: Mar. 23, 1977

Related U.S. Application Data

[62] Division of Ser. No. 677,480, April 15, 1976, Pat. No. 4,039,736.

[51] Int. Cl.$^2$ .............................. C12D 9/14
[52] U.S. Cl. ...................... 195/96
[58] Field of Search ................ 195/80 R, 96

[56] References Cited

U.S. PATENT DOCUMENTS

| 3,092,550 | 6/1963 | Gaeumann et al. | 536/17 |
|---|---|---|---|
| 3,590,028 | 6/1971 | Arcamone et al. | 536/17 |
| 3,616,242 | 10/1971 | Bellor et al. | 195/80 R |
| 3,686,163 | 8/1972 | Arcamone et al. | 536/17 |
| 3,803,124 | 4/1974 | Arcamone et al. | 536/17 |
| 3,864,480 | 2/1975 | Wang et al. | 424/120 |
| 3,988,315 | 10/1976 | Umezawa et al. | 536/17 |
| 4,039,736 | 8/1977 | Nettleton, Jr. et al. | 536/17 |

FOREIGN PATENT DOCUMENTS

| 2,362,707 | 3/1970 | Germany | 536/17 |
|---|---|---|---|
| 846,130 | 8/1960 | United Kingdom | 536/17 |
| 901,830 | 7/1962 | United Kingdom | 536/17 |
| 985,598 | 3/1965 | United Kingdom | 536/17 |
| 1,003,383 | 9/1965 | United Kingdom | 536/17 |
| 1,188,262 | 4/1970 | United Kingdom | 536/17 |
| 1,241,750 | 8/1971 | United Kingdom | 536/17 |

OTHER PUBLICATIONS

Brockmann et al., "Chem. Ber.", No. 92, 1959, pp. 1904–1909.
Ettlinger et al., "Chem. Abst.", vol. 54, 1960, pp. 1465(i)–1468(i).
Gottlieb et al., "Antibiotics", vol. I, 1967, pp. 190–210.
Keller-Schierlein et al., "Antimicrobial Agents and Chemotherapy", 1970, p. 68.
Fleck et al., "Antimicrobial Agent and Chemotherapy", vol. I, No. 5, pp. 385–391.
Biochemistry Research, 10-10-73, pp. 33–34.
Brazhnikova et al., "The Journal of Antibiotics", vol. XXVII, No. 4, pp. 254–259.
Wani et al., "Jour. Amer. Chem. Soc.", vol. 97, No. 20, 10-1-75, pp. 5955–5956.

*Primary Examiner*—Raymond N. Jones
*Assistant Examiner*—Robert J. Warden
*Attorney, Agent, or Firm*—David M. Morse

[57] ABSTRACT

A novel anthracycline antibiotic complex designated herein as bohemic acid complex is produced by fermentation of Actinosporangium sp. A.T.C.C. 31127. The complex and two bioactive components designated marcellomycin and musettamycin exhibit antibiotic activity and inhibit the growth of various tumor systems in rodents.

2 Claims, No Drawings

ANTIBIOTIC COMPOUNDS MARCELLOMYCIN AND MUSETTAMYCIN

CROSS-REFERENCE TO RELATED APPLICATION

This is a divisional application of co-pending Ser. No. 677,480 filed Apr. 15, 1976, now U.S. patent No. 4,039,736.

BACKGROUND OF THE INVENTION

1. Field of the Invention

This invention relates to new anthracycline antibiotics and to their production and recovery.

2. Description of the Prior Art

A number of anthracycline glycosides have been described in the literature. Among them, daunomycin and adriamycin are particularly being watched with keen interest in the field of cancer chemotherapy and have already been applied clinically for human cancers.

Preparation of adriamycin by fermentation of *S. peuceticus var. caesius* is disclosed in U.S. Pat. No. 3,590,028. Chemical conversion of daunomycin to adriamycin is taught in U.S. Pat. No. 3,803,124.

Daunomycin (produced by fermentation of *S. peuceticus* in U.K. Pat. No. 1,003,383) may be the same as Rhone-Poulenc's 13,057 R.P. (formerly rubidomycin and now daunorubicin; see U.K. Pat. Nos. 985,598, 1,188,262 and 1,241,750 and U.S. Pat. No. 3,616,242) and is probably identical to Ciba's danubomycin disclosed in U.S. Pat. No. 3,092,550 and U.K. Pat. No. 901,830. See also U.S. Pat. No. 3,686,163 on dihydrodaunomycin.

Cinerubin A and cinerubin B, glycosides of the aglycone $\epsilon$-pyrromycinone, are disclosed in U.K. Pat. No. 846,130 [see also U.S. Pat. No. 3,864,480 and Keller-Schierlein, et al., Antimicrobial Agents and Chemotherapy, page 68 (1970) and Chemical Abstracts, 54, 1466i (1960)].

The anthracycline glycoside carminomycin described in J. Antibiotics 27:254–259 (1974), in West German Specification 2,362,707 and in J. Amer. Chem. Soc. 97(20):5955–5956 (1975) has been reported to be active against several animal tumor systems.

Trypanomycin is described in Antimicrobial Agents and Chemotherapy 1:385–391 (1972) as having strong antiprotozoal activity. It has an aglycone similar to but not identical with $\epsilon$-pyrromycinone.

The antibiotic pyrromycin disclosed in Chem. Ber. 92:1904–1909 (1959) contains the aglycone $\epsilon$-pyrromycinone and the glycosidic sugar rhodosamine.

For further illustrative and summary disclosures of anthracycline antibiotics see Index of Antibiotics from Actinomycetes, Hamao Umezawa, Editor-in-Chief, University Park Press, State College, Pennsylvania, U.S.A. (1967) as follows:

| Antibiotic | Page Number |
| --- | --- |
| Aklavin | 111 |
| Cinerubin A | 220 |
| Cinerubin B | 221 |
| Danubomycin | 242 |
| Daunomycin | 243 |
| Pyrromycin | 542 |
| Rhodomycin A,B | 561 |
| Rubidomycin | 574 |

The textbook Antibiotics, Volume 1, Mechanism of Action, edited by David Gottlieb and Paul D. Shaw, SpringerVerlag New York, Inc., N.Y., N.Y. (1967) at pages 190–210 contains a review by A. DiMarco entitled Daunomycin and Related Antibiotics.

Information Bulletin, No. 10, International Center of Information of Antibiotics, in collaboration with WHO, December, 1972, Belgium, reviews anthracyclines and their derivatives.

SUMMARY OF THE INVENTION

This invention relates to novel anthracycline antibiotic substances. More particularly, it relates to an anthracycline antibiotic complex designated herein as bohemic acid complex, said complex being produced by cultivating a bohemic acid-producing strain of Actinosporangium sp., most preferably Actinosporangium sp. A.T.C.C. 31127, in an aqueous nutrient medium containing assimilable sources of nitrogen and carbon under submerged aerobic conditions until a substantial amount of said bohemic acid complex is produced by said organism in said culture medium and optionally recovering the complex from the culture medium. Also provided by the present invention are two novel bioactive anthracycline components of bohemic acid complex, said components being designated herein as musettamycin and marcellomycin. The components may be recovered from the fermentation broth by extraction of the whole fermentation broth with a water-immiscible organic solvent followed by separation and isolation of the individual antibiotic compounds as by chromatographic procedures. The bohemic acid complex and its bioactive components exhibit both antibacterial and antitumor activity.

DETAILED DESCRIPTION

Bohemic acid complex and its components marcellomycin and musettamycin may be produced by fermentation of a new member of the genus Actinosporangium designated Actinosporangium sp. strain C-36,145. The above organism was obtained from a soil sample taken from Ontario, Canada. A culture of the organism has been deposited in the American Type Culture Collection, Washington, D.C., and added to its permanent collection of microorganisms as A.T.C.C.31127.

As in the case of many antibiotic-producing cultures, fermentation of Actinosporangium sp. strain C-36,145, A.T.C.C. 31127, results in the production of a mixture or complex of component substances. Two bioactive anthracycline components, musettamycin and marcellomycin, have been separated from the bohemic acid complex produced by the abovementioned organism.

Musettamycin and marcellomycin have been determined to have the following structural formulae:

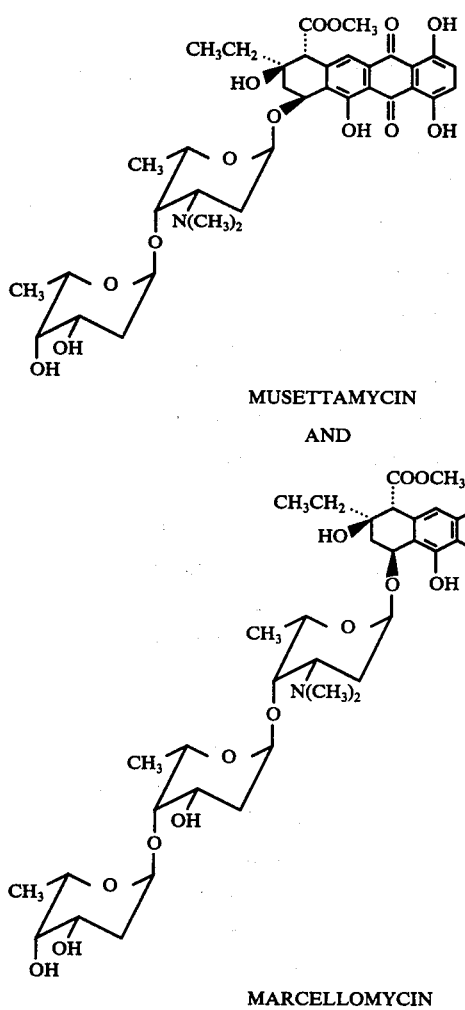

MUSETTAMYCIN

AND

MARCELLOMYCIN

As shown, both of the above components are anthracycline glycosides of the aglycone ε-pyrromycinone. Musettamycin contains two glycosidic sugar units, i.e. 2-deoxy-L-fucose and L-rhodosamine, while marcellomycin contains two units of 2-deoxy-L-fucose and one L-rhodosamine unit. The structures of the components were determined by analysis of their infrared and nuclear magnetic resonance spectra and are in agreement with the physical data provided below.

In the above formulae the dotted lines indicate that the bonded group is partially located below the plane of the ring to which it is attached. The spikes indicate that the attached group is positioned above the plane of the ring.

The bohemic acid complex and the individual musettamycin and marcellomycin components form salts with both acids and bases, and the pharmaceutically acceptable salts of the complex and components are included within the scope of the present invention. Examples of such pharmaceutically acceptable salts include salts with stronger acids such as hydrochloric, hydrobromic, sulfuric, nitric and phosphoric and with metallic cations, e.g. alkali metal or alkaline earth metal cations such as sodium, potassium, calcium and magnesium.

Preparation of the novel anthracycline antibiotics of the present invention is described below.

THE MICROORGANISM

The strain C-36,145 has the following morphological characteristics. The strain forms a sporangium-like body (false sporangium) on the tip of the sporophore, which is an agglomeration of a thickly coiled sporechain. The sporechain often interlaces with the neighboring aerial hyphae, and it develops to the sporangium-like structure covered by a viscid material. The sporangium-like body and aerial mycelium are formed on glucose-asparagine agar, tyrosine agar, yeast extract-malt extract agar and oat meal agar. In addition to the formation of a large number of false sporangia, there are also produced ordinary spore-chains, though much less in number, which form open spirals. Spores in the sporangium-like body are smooth in surface, ellipsoidal in shape and non-motile. Spores in the ordinary spore-chain are of oval shape and have a smooth or occasionally warty surface. Primary mycelium is branched, non-septated and non-fragmented.

Table 1 reports the cultural properties obtained on various media. Strain C-36,145 grows well on most of the agar media tested, but the formation of aerial mycelium and the sporulation are somewhat slow. Mass color of the aerial mycelium is light greenish gray. Reverse side of the growth is reddish orange to red in glucose-asparagine agar, inorganic salts-starch agar, yeast extract-malt extract agar and oat meal agar. It produces melanoid pigment in tyrosine agar and peptone-yeast extract-iron agar.

The physiological characteristics and carbohydrate utilization of strain C-36,145 are shown in Tables 2 and 3, respectively. The growth temperature ranged from 20° to 37° C. and no proliferation was seen at 43° C.

Strain C-36,145 contains LL-diaminopimelic acid (LL-DAP) and glycine as characteristic amino acid components in the cell wall. Diagnostic carbohydrate was not present.

The morphological, cultural and physiological characteristics of Strain C-36,145 are similar to those of the genus Streptomyces except for the formation of sporangium-like body. The cell wall composition is also similar to that of the type I group (Streptomyces type) according to the classification of Lechevalier and Lechevalier in Int. J. Syst. Bacteriol. 20:435–443 (1970). The sporangium-like body of strain C-36,145 appears to be different from the normal sporangium produced by the well-defined sporangiumforming genera in that (1) the latter form small sporangia at an early stage of the growth which mature with time and (2) ordinary sporangia are usually not covered by a viscous material.

Krassilnikov and Tsi-Shen proposed in 1961 a new genus of Actinosporangium in the family Actinoplanaceae (later transferred to the family Streptosporangiaceae) for the organism producing a spore mass which was very similar to sporangium (Isv. Akad. Navk. USSR, Ser. Biol., 113–116, 1961). Subsequently, the sporangium-like body was found to be a viscid spore-forming mass and different from the real sporangium, and the genus Actinosporangium was placed in the family Streptomycetaceae on the basis of its morphological characteristics and the cell wall composition of the type I group.

Thus, on the basis of all the available data, Strain C-36,145 is considered to be a new species of the genus Actinosporangium. It should be noted, however, that only two species in the genus Actinosporangium have been reported in the literature and hence the genus has not yet been fully established (see H. Prauser: The Actinomycetales. The Jena Intl. Sym. on Taxonomy. Sept., pp. 329–335, 1968. Veb. Gustav Fischer Verlag, JENA, 1970).

It is to be understood that the present invention is not limited to use of the particular Strain C-36,145 or to organisms fully answering the above descriptions. It is especially intended to include other bohemic acid-producing strains or mutants of the said organism which can be produced from the described organism by various means including x-radiation, ultraviolet radiation, treatment with nitrogen mustards, phage exposure, and the like.

Table 1.

Cultural Characteristics of Strain C-36,145

| | Growth | Reverse Color | Aerial Mycelium | Diffusible pigment |
|---|---|---|---|---|
| Sucrose-nitrate agar | Moderate | Yellowish pink | Scant, whitish | None |
| Glucose-asparagine agar | Good | Reddish orange to red | Abundant, greyish leaf | None or reddish orange |
| Glycerol-asparagine agar | Good | Rose | Moderate, light grey to pale pink | None or reddish pink |
| Inorganic salts-starch agar | Moderate | Reddish orange to deep red | Poor, greyish leaf | Light orange, partially light yellow |
| Tyrosine agar | Good | Brown to deep purplish-brown | Poor, greyish leaf | Dark brown |
| Nutrient agar | Poor | Colorless | None | None |
| Yeast extract-malt extract agar | Good | Deep red | Moderate, greyish leaf partially greyish pink | Light brown |
| Oat meal agar | Moderate | Vivid reddish orange | Moderate, greyish leaf | Vivid orange |
| Peptone-yeast extract-iron agar | Moderate | Black | None | Black |

Table 2.

Physiological Characteristics of Strain C-36,145

| Tests | Responses | Methods and Materials Employed |
|---|---|---|
| Nitrate reduction in inorganic medium | Strongly positive | Czapek's sucrose nitrate broth |
| Nitrate reduction in organic medium | Strongly positive | Nitrate medium, consisted of yeast yeast extract 0.5%, glucose 1.0%, $KNO_3$ 0.5% and $CaCO_3$ 0.1%. |
| Skim-milk agar | Abundant growth. Negative hydrolysis. Deep yellowish-red to deep reddish-purple mycelial pigment. | Leudeman's medium [Intl. L. Syst. Bacteriol. 21:240–247 (1971)] |
| 10% Skim-milk solution | Brownish broth color. Reddish-orange ring growth. No peptonization nor coagulation. | |
| Gelatin slab | Rapid and complete liquefaction. | Basal medium: Yeast extract 0.4% malt extract 1.0% and glucose 0.4%. |
| Melanin formation | Strongly positive | Tyrosine agar and peptone-yeast extract-iron agar. |
| Growth-temperature | Optimal growth at 28° C. Moderate growth at 20–37° C. Slow growth at at 15° C. No growth at 10° C. and 43° C. | Yeast extract-malt extract agar. |
| NaCl tolerance | Moderate growth at 0.5–4%-NaCl. No growth at 8%-NaCl. | Basal medium: 1%-yeast extract, 2%-soluble starch and 1.5% agar. |

Table 3.

Carbohydrate Utilization of Strain C-36,145

| | |
|---|---|
| D(−)-Arabinose | − |
| L(+)-Arabinose | ++ |
| D-Xylose- | ++ |
| D-Ribose | ++ |
| L-Rhamnose | ++ |
| D-Glucose | ++ |
| D(+)-Galactose | ++ |
| D-Fructose | ++ |
| D-Mannose | ++ |
| Sucrose- | ++ |
| Maltose | ++ |
| Lactose | ++ |
| D(+)-Melibiose | ++* |
| Raffinose | ++* |
| D(+)-Melezitose | − |
| Soluble starch | ++ |
| Cellulose | − |
| Glycerol | ++ |
| Inositol | ++ |
| D-Mannitol | ++* |
| Sorbitol | − |
| Dulcitol | − |

Basal medium: Pridham-Gottlieb medium
*Rich production of reddish-orange pigment

Preparation of Bohemic Acid Complex

Bohemic acid complex may be produced by cultivating a bohemic acid-producing strain of Actinosporangium sp. having the characteristics of A.T.C.C. 31127 or a mutant thereof under submerged aerobic conditions in an aqueous nutrient medium. The organism is grown in a nutrient medium containing on assimilable carbon source, for example an assimilable carbohydrate. Examples of suitable carbon sources include sucrose, lactose, maltose, mannose, fructose, glucose, glycerol and soluble starch. The nutrient medium should also contain an assimilable nitrogen source such as fish meal, peptone, soybean flour, peanut meal, cotton seed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of the bohemic acid complex can be effected at any temperature conductive to satisfactory growth of the organism, e.g. 20°–37° C., and is conveniently carried out at a temperature of about 27° C.

The medium normally is slightly alkaline, but the exact pH can be varied widely depending on the particular medium used.

The fermentation may be carried out in Erlenmeyer flasks or in laboratory or industrial fermentors of various capacities. When tank fermentation is to be used, it is desirable to produce a vegetative inoculum in a nutrient broth by inoculating a small volume of the culture medium with the spore form of the organism. After obtaining an active inoculum in this manner, it is transferred aseptically to the fermentation tank medium for large scale production of the antibiotics. The medium used for the vegetative inoculum can be the same as that employed for larger fermentations, although other media can be employed.

As is customary in aerobic submerged culture processes, sterile air is blown through the culture medium. Agitation may be maintained by means of agitators generally familiar to those in the fermentation industry.

In general, optimum production of the bohemic acid complex is achieved after incubation periods of about 190–210 hours in stir-jar fermentors or tank fermentors. The course of the fermentation can be followed by assaying the fermentation medium from time to time against an organism susceptible to the bohemic acid complex, e.g. *D. pneumoniae, St. pyrogenes* or *S. aureus.*

The bohemic acid complex may be recovered from the fermentation medium by extraction with a water-immiscible organic solvent, preferably a polar organic solvent such as ethyl acetate, methyl isobutyl ketone or a (higher)alcohol (e.g. n-butanol), and most preferably methyl isobutyl ketone. The majority of the antibiotic activity is found in the broth, and thus the broth may be filtered prior to extraction. In the preferred procedure, however, the whole fermentation broth is extracted with the organic solvent at a pH of between about 7.5 and 8.5. The organic phase may then be filtered and dried to give the solid bohemic acid complex. Alternatively, the organic extract may be concentrated and the solid complex precipitated by dilution with a suitable antisolvent such as Skellysolve B.

SEPARATION AND ISOLATION OF MUSETTAMYCIN AND MARCELLOMYCIN

The anthracycline antibiotics musettamycin and marcellomycin can be separated from each other and from the other components of bohemic acid complex by chromatography of solutions of bohemic acid complex on columns packed with a suitable adsorbent such as Sephadex LH 20 (trade name for dextran derivatives used as gel filtrants in organic solvents; manufactured by Pharmacia Fine Chemcicals, Inc.). The bohemic acid complex components are then eluted from the adsorbent with a suitable organic solvent such as chloroform.

Multiple fractions are collected and, with suitable dilution, their adsorbancies are determined at 490 m$\mu$. The latter are plotted graphically against the corresponding fraction numbers to determine peaks for the components eluted from the column. The appropriate fractions, as determined from the elution sequence are combined and evaporated to give the solid individual antibiotics. The solids may be partially purified by recrystallization from a suitable organic solvent such as acetonitrile, chloroform-Skellysolve B or methanol.

The musettamycin and marcellomycin components may be further purified by use of the high pressure liquid chromatography procedure described in detail in Examples 10 and 11. This procedure has been found to give extremely pure samples of the two antibiotics.

Bohemic acid complex or its musettamycin and marcellomycin components can be converted by methods known per se to the pharmaceutically acceptable salts described above.

Biological Activity Data

The in vitro minimum inhibitory concentration (MIC) of musettamycin and marcellomycin were determined for a number of microorganisms using the standard tube dilution procedure.

Table 4.

| Antimicrobial Spectrum of Musettamycin and Marcellomycin | | | |
|---|---|---|---|
| Test Organism | | MIC in $\mu$g/ml. Mar. | Mus. |
| Bacteria: | | | |
| *Streptococcus pneumoniae* | A-9585 | .03 | .06 |
| *Streptococcus pyogenes* | A-9604 | .03 | .06 |
| *Staphylococcus aureus* | A-9497 | 1 | 0.5 |
| *Staphylococcus aureus* | A-9537 | 1 | 1 |
| *Escherichia coli* | A-15119 | 125 | >125 |
| *Escherichia coli* | A-21780 | 32 | 32 |
| *Klebsiella pneumoniae* | A-9977 | 125 | >125 |
| *Proteus mirabilis* | A-9900 | >125 | >125 |
| Fungi: | | | |
| *Candida albicans* | A-9540 | 125 | 125 |
| *Candida tropicalis* | A-15051 | 125 | 63 |
| *Candida krusei* | A-15052 | 125 | 125 |
| *Cryptococcus neoformans* | A-1503 | 125 | 63 |
| *Trichophyton mentagrophytes* | A-9870 | >125 | >125 |

Mar. = Marcellomycin
Mus. = Musettamycin

The acute intraperitoneal $LD_{50}$ in mice is 9.8 to 21.12 mg./kg. for musettamycin and 6.35 to 10.56 mg./kg. for marcellomycin.

The compounds of the present invention were also tested against various transplantable rodent tumor systems. Details of the methods used have been described in Cancer Chemoth. Reports 3:1–87 (Part 3), 1972.

The first observation of tumor inhibitory effects was with the Walker 256 carcinosarcoma implanted as a solid intramuscular tumor in rats. Treatment of the animals with fermentation broth containing bohemic acid complex caused 73% inhibition of tumor growth compared to untreated control tumors.

Typical effects of therapy with partially purified musettamycin on two lymphatic leukemias in mice, i.e. P-388 and L-1210, are shown below in Table 5. Significant tumor inhibition over a 16 fold dose range was observed with P-388 leukemia.

Table 5:

Effect of Musettamycin on Transplanted Mouse Leukemias

| | P-388 (ascitic) | | | L-1210 (ascitic) | | |
|---|---|---|---|---|---|---|
| Dose mg/kg | Ave. wt. Difference (T-C, g.) | T/C Percent MST | Survivors Day 5 | Avg. wt. Difference (T-C, g.) | T/C Percent MST | Survivors Day 5 |
| 6.4 | −3.4 | 160 | 6/6 | −2.5 | 140 | 6/6 |
| 3.2 | −3.0 | 145 | 6/6 | −2.5 | 120 | 5/6 |
| 1.6 | −2.8 | 145 | 6/6 | −1.3 | 133 | 6/6 |
| .8 | −2.0 | 140 | 6/6 | −1.1 | 107 | 6/6 |
| .4 | −1.6 | 135 | 6/6 | — | — | — |
| .2 | −2.1 | 120 | 6/6 | — | — | — |

Treatment: Single injection Day 1 intraperitoneally.
Evaluation: T/C percent MST = median survival time in days: Treated/Control × 100. T/C > 125 considered significant prolongation of host survival.

Purified musettamycin and marcellomycin (as prepared by the procedures described in Examples 10 and 11 below) were tested against L-1210 mouse leukemia and the results are shown in Table 6. These data indicate that marcellomycin is about four times as potent as musettamycin in its inhibitory effects on this tumor.

The antibiotic compounds of the present invention including bohemic acid complex, its components musettamycin and marcellomycin, and salts and mixtures thereof, exhibit both antimicrobial and antitumor activity. The invention includes within its scope pharmaceutical compositions containing at least one of such antibiotic substances mentioned above with a compatible pharmaceutically acceptable carrier. The compositions may also contain other active antibacterial and/or antitumor agents. The compositions may be made up in any pharmaceutical form appropriate for the route of administration in question. Examples of such compositions include solid compositions for oral administration such as tablets, capsules, pills, powders and granules, liquid compositions for oral administration such as solutions, suspensions, syrups and elixers and preparations for parenteral administration such as sterile solutions, suspensions or emulsions.

Table 6.

Effect of Bohemic Acid Products L-1210 Leukemia

| Compound | Dose mg/kg/day | Day of Treatment | Total Injections | MST Days | Effect MST % T/C | Average Weight Change in g. | Survivors Day 5 |
|---|---|---|---|---|---|---|---|
| Mus. | 12.8 | 1 | 1 | 10.5 | 150 | −0.6 | 6/6 |
| | 6.4 | 1 | 1 | 10.0 | 143 | +0.5 | 6/6 |
| | 3.2 | 1 | 1 | 9.0 | 129 | +0.3 | 6/6 |
| | 1.6 | 1 | 1 | 9.0 | 129 | +0.3 | 6/6 |
| | .8 | 1 | 1 | 8.5 | 121 | +1.2 | 6/6 |
| | .4 | 1 | 1 | 8.0 | 114 | +1.3 | 6/6 |
| Mus. | 6.4 | 1→5 | 5 | 6.0 | 86 | −1.5 | 5/5 |
| | 3.2 | 1→5 | 5 | 11.0 | 157 | −1.3 | 6/6 |
| | 1.6 | 1→5 | 5 | 10.0 | 143 | +0.3 | 6/6 |
| | .8 | 1→5 | 5 | 9.5 | 136 | +0.4 | 6/6 |
| | .4 | 1→5 | 5 | 9.0 | 129 | +0.6 | 6/6 |
| | .2 | 1→5 | 5 | 9.0 | 129 | +1.8 | 6/6 |
| Mar. | 12.8 | 1 | 1 | 10.0 | 143 | −0.7 | 3/6 |
| | 6.4 | 1 | 1 | 11.0 | 157 | −0.7 | 6/6 |
| | 3.2 | 1 | 1 | 11.0 | 157 | −0.7 | 6/6 |
| | 1.6 | 1 | 1 | 10.0 | 143 | −0.1 | 6/6 |
| | .8 | 1 | 1 | 10.5 | 150 | 0 | 6/6 |
| | .4 | 1 | 1 | 9.0 | 129 | −0.8 | 6/6 |
| Mar. | 6.4 | 1→5 | 4 | TOXIC | TOXIC | TOXIC | 0/6 |
| | 3.2 | 1→5 | 5 | 6.0 | 86 | −1.2 | 3/6 |
| | 1.6 | 1→5 | 4 | 6.0 | 86 | −0.1 | 3/6 |
| | .8 | 1→5 | 5 | 10.0 | 143 | −0.2 | 6/6 |
| | .4 | 1→5 | 5 | 9.0 | 129 | 0 | 6/6 |
| | .2 | 1→5 | 5 | 9.0 | 129 | −1.1 | 6/6 |
| Control | Saline | 1→5 | 5 | 7.0 | — | +3.0 | 10/10 |

Inoculum: $10^6$ ascitic cells, i.p. into BDF$_1$ female mice
Treatment: i.p. in 0.5 ml. volume
Evaluation: MST = median survival time in days; %T/G = MST treated/MST control × 100.
Criteria: T/C > 125 considered significant tumor inhibition (prolongation of host survival)
Mus. = Musettamycin
Mar. = Marcellomycin For use as an antibacterial agent the compositions are administered so that the concentration of active ingredient is greater than the minimum inhibitory concentration for the particular organism being treated. A suggested dosage for use as an antitumor agent in mammalian species is 2.5 to 10 mg./M² for a single injection intravenous treatment course with marcellomycin and 10 to 40 mg./M² for a single intravenous treatment with musettamcyin.

The following examples serve to illustrate the invention without limiting it. μSTYRAGEL, phenyl/CORASIL and phenyl/PORASIL B are tradenames of Waters Associates, Inc. for gel permeation chromatographic packing materials produced by chemically bonding organo-silanes to silica. Sephadex LH-20 is the tradename of Pharmacia Fine Chemicals, Inc. for a modified cross-linked dextran used in adsorption and gel filtration chromatography.

EXAMPLE 1

Shake-flask fermentation

The organism Actinosporangium sp. Strain C-36,145 (A.T.C.C. 31127) is grown on an agar slant medium consisting of 2 g. D-glucose, 20 g. oatmeal, 2 g. soy peptone and 2 g. agar made up to one liter with distilled water. After at least 6 days growth at 27° C., spores are transferred to a 500 ml. Erlenmeyer flask containing 100 ml. of sterile medium consisting of 30 g. D-glucose, 10 g. soybean flour, 10 g. Pharmamedia (Traders Oil Mill Co., Fort Worth, Texas) and 3 g. $CaCO_3$ made up to one liter with distilled water. This vegetative culture is incubated at 27° C. on a Gyrotary tier shaker (Model G53, New Brunswick Scientific Co., Inc.) set at 210 rev./min. describing a circle with a 5.1 cm. diameter. After 48 hours four milliliters of culture are transferred to a 500 ml. Erlenmeyer flask containing 100 ml. of sterile production medium consisting of 50 g. glycerol, 20 g. soybean flour, 10 g. peanut meal and 10 g. $CaCO_3$ made up to one liter with distilled water. The culture is incubated at 27° C. for 144 hours on a shaker set at 230 rev./min. At this time antibiotic activity consisting of the bohemic acid complex is found in the culture filtrate and mycelium.

EXAMPLE 2

Stir-jar fermentation

Bohemic acid complex is produced in stir-jar fermentors with the use of a 48 hour old vegetative culture as described in Example 1. Four hundred milliliters of culture is transferred to 10 liters of sterile production medium as described in Example 1 including 0.01% Hodag Fl silicone antifoam (Hodag Chemical Corp., Skokie, Ill.) contained in a 14 liter capacity stir-jar. The stir-jar is installed in a Fermentor Drive Assembly (Model FS-614, New Brunswick Scientific Co., Inc., New Brunswick, N.J.). The temperature is maintained at 27° C., the air flow rate is 6 liters/min. and the agitator is set at 300 r.p.m. Hodag Fl antifoam is fed automatically as required to control foaming. At approximately 210 hours the incubation is terminated and bohemic acid complex is found in the culture filtrate and the mycelium.

EXAMPLE 3

Tank fermentation

A tank fermentor with 37.8 liters of sterile production medium (as in Example 1) is inoculated with 1.89 liters of vegetative culture (as prepared in Example 1), agitated with an impeller speed of 300 r.p.m., aerated at 85 liters/min. and incubated at 27° C. for 190 hours. The bohemic acid complex is found in the culture filtrate and mycelium.

EXAMPLE 4

Tank fermentation

A tank fermentor with 3028 liters of production medium (as in Example 1) is inoculated with 152 liters of vegetative culture (as prepared in Example 1), agitated with an impeller speed of 155 r.p.m., aerated at 141.6 liters/min. and incubated at 27° C. for 190 hours. At this time the presence of bohemic acid complex is found in the culture filtrate and mycelium.

EXAMPLE 5

Isolation of bohemic acid complex

Whole fermentation broth (7 liters) at its harvest pH 8.1, was stirred with about an equal volume of methyl isobutyl ketone for 20–30 min. A large amount of diatomaceous earth filter aid was then added and, after stirring thoroughly to mix this in, the mixture was filtered on a filter aid mat using vacuum suction. The filtrate separated into two phases of which the lower(aqueous) was discarded. The organic phase was evaporated under vacuum to a small volume (50–100 ml.) and diluted with Skellysolve B (tradename for a petroleum ether fraction of b.p. 60°–68° C. consisting essentially of n-hexane and sold by Skelly Oil Co.) to precipitate a dark red solid which was dried in vacuo to give 1.9 g. of bohemic acid complex.

EXAMPLE 6

Isolation of bohemic acid complex on a large scale

Whole fermentation broth (3,000 liters) at pH 8.0–8.5 was chilled at 25° C. and agitated vigorously with 3,000 liters methyl isobutyl ketone for 30 min. at 20°–30° C. To the emulsion was added 360 kg. filter aid and the mixture was stirred vigorously for another hour. It was then allowed to settle for about 30 min. after which 2,300–2,500 liters or organic phase was decanted and chilled at 0°–10° C. An additional 800 liters methyl isobutyl ketone was agitated with the mixture for 20 min., decanted after settling 30 min., and combined with the chilled first fraction to give a total extract volume of 3,300–3,400 liters. This was polish filtered to give a final 3,100–3,200 liter methyl isobutyl ketone extract free of solids and insoluble aqueous phase. The organic extract was vacuum concentrated at 0°–10° C. to a final volume of 6 liters. This was added to 60 liters Skellysolve B with stirring at 20°–25° C. The precipitated solids were collected on a Nutsche filter, washed with 10 liters Skellysolve B and sucked dry to give 900–1,000 g. somewhat oily and dark red amorphous product. This was stirred with excess ether, filtered on a Buchner funnel, rinsed with additional ether, sucked dry and dried in vacuo to give 351 g. amorphous dark red bohemic acid complex.

EXAMPLE 7

Fractionation of bohemic acid complex

Sephadex LH-20 soaked for 68 hours in chloroform was slurry packed into a Pharmacia SR 25/100 column (25 mm. I.D. × 100 cm. height) equipped with adjusted teflon tips at each end. The column was packed so as to be completely filled from tip to tip, an effective bed height of 90–95 cm. Bohemic acid complex (500 mg.) was dissolved in 10 ml. chloroform and applied to the column which was then allowed to develop with chloroform by downflow at a take-off rate of 1 ml./min. Eluted liquid was collected in 6 ml. cuts in a fraction collector. Samplings of even numbered tubes were diluted 80-fold with chloroform and read in a Bausch and Lomb Spectronic 20 colorimeter at 490 m$\mu$. Four distinct bands of anthracycline pigments were noted as follows:

| Tube No. | Wgt. upon Evaporation |
|---|---|
| 1–4 | — |

-continued

| Tube No. | | Wgt. upon Evaporation |
|---|---|---|
| 5–11 | First Band | 66 mg. |
| 12–14 | — | |
| 15–21 | Second Band | 36 mg. |
| 22–35 | — | |
| 36–44 | Third Band | 18 mg. |
| 45 | — | |
| 46–57 | Fourth Band | 48 mg. |
| 58– | — | |

The solids obtained were chromatographed on Brinkmann 60F254 silica gel thin layer plates using an 80:20 toluene:methanol solvent system. The first band to elute was shown by thin layer chromatography to be a complex inactive mixture. The second band gave a characteristic pinkish red zone at about $R_f = 0.75$. This fraction was also inactive and was found to comprise mainly η-pyrromycinone. The third fraction to elute gave a single zone with $R_f \sim 0.3$. This was determined to be musettamycin and was highly active when tested on both the L-1210 and P-388 mouse leukemia systems. The final band to elute gave a zone at $R_f \sim 0.3$ and comprised mainly marcellomycin. This component also exhibited high activity when tested on the two mouse leukemias. Although both musettamycin and marcellomycin on thin-layer chromatography have $R_f$ values around 0.3, musettamycin moves slightly faster. When mixed, musettamycin and marcellomycin are resolved then into two very close zones of color.

EXAMPLE 8

Large scale fractionation

A 6 (diameter) × 77 inches (height) glass column was equipped at the base with a no clog filter on top of which was placed a layer of glass wool followed by a circular polyethylene frit. The latter was cut to a diameter of 5⅜ inches to allow for swelling in chloroform. Sephadex LH-20 (8.73 kg.) was stirred for 3 hours in chloroform, filtered, and the solid reslurried in chloroform and left to stand for 16 hours. The mixture was then agitated for 15 min. and loaded onto the column. A 30 g. sample of bohemic acid complex (prepared as in Example 6) was heated with 1.5 liters of chloroform for 15 min. and then stirred for 16 hours. Upon filtration, 7.5 g. of undissolved material containing some activity was separated. (In later runs it was found that the sample could be completely dissolved in chloroform containing 30–40% methanol. Chromatographic results were the same with this procedure). The filtrate was applied to the column and downward development begun with chloroform. A flow rate of 16 ml./min at takeoff was maintained throughout the run. An initial volume of 1,445 ml. of eluant was taken before color reached the bottom of the gel bed. At this point collection of 100 ml. fractions was initiated and continued until the liquor was quite light again, a total of 906 cuts. Aliquots of every fifth fraction were diluted and analyzed as described in Example 7. Four components were seen to have separated as indicated below.

| Fraction | Description | Wgt. upon Evaporation |
|---|---|---|
| 1–20 | 1st component, mixture*, inactive | 6.74 g. |
| 21–44 | 2nd component, mixture, inactive** | 4.18 g. |
| 45–53 | trough - discarded | 385 mg. |
| 54–70 | 3rd component, single | 1.45 g. |

-continued

| Fraction | Description | Wgt. upon Evaporation |
|---|---|---|
| | compound-musettamycin, active | |
| 71–75 | trough - discarded | 198 mg. |
| 76–110 | 4th component, mixture comprising mainly marcellomycin, active | 4.03 g. |
| 111–200 | post cut | 1.72 g. |

*as evidenced by thin layer chromatography
**mainly η-pyrromycinone

EXAMPLE 9

Partial purification of musettamycin

The solid (421.4 mg.) obtained from the third component of Example 8 was dissolved in excess boiling chloroform and the solution filtered hot through fluted filter paper. The filtrate was boiled down to <20 ml. on a steam bath. Skellysolve B was then added dropwise to the warm solution until the cloud point was reached followed by addition of several drops of chloroform. After being allowed to cool to ambient temperature, the mixture was placed in a freezer at −20° C. overnight. The deep red crystalline platelets were collected and dried in vacuo to give 358 mg. musettamycin, m.p. 162°–163° C.

EXAMPLE 10

Purification of Musettamycin

Crude ethylenediamine tetraacetic acid (EDTA) - washed musettamycin was passed over a four column bank of μ STYRAGEL (tradename for a gel filtrant column packing material used in gel permeation chromatography; the material consisting of small beads, 8–10 microns in diameter, composed of rigid, cross-linked polymers of styrene divinylbenzene; and manufactured by Waters Associates, Inc.) (500-100-100-100 A) with chloroform as a mobile phase at a flow rate of 0.7 ml./min. for an initial clean-up. Nine runs of 100 mg. each were made. The elution was monitored with the aid of a refractive index detector (Waters Associates) and in each run the main peak eluting at 37.5–45 min. was collected. The main fraction from the nine runs was combined and evaporated to dryness in vacuo. The dark red amorphous solid (660 mg.) was dissolved in 22 ml. of a 45:55 solvent mixture of acetonitrile:0.01 M sodium acetate, pH 4.0. The mixture was centrifuged to remove a small amount of suspended material and the clear supernatant transferred to a sealable penicillin vial. A portion (1.25 ml., ~ 37 mg.) of the dark red solution was loaded into a U6K injector (Waters Associates, Inc.) and the sample then loaded onto the column. The sample was chromatographed on a 1 meter × 4.6 mm. I.D. stainless steel column packed with phenyl/-PORASIL B (tradename for a bonded phase material for partition chromatography manufactured by Waters Associates, Inc.; composed of a totally porous silica having liquid diphenyl dichlorosilane chemically bonded to the silica) (37–75 μ particle size). The mobile phase consisted of a 35:65 acetonitrile:0.01 M sodium acetate pH 4.0 mixture at a flow rate of 1.9–2.0 ml./min. The elution was monitored using a refractive index monitor. Fractions were collected at 75 sec. intervals with the aid of an automatic fraction collector (Scientific Manufacturing Industries). One hundred and twenty tubes were collected and the column was washed at a flow rate of 3.0 ml./min. with methanol for 15 min., water for 15 min. and acetonitrile:0.01 M sodium acetate pH 4 mixture (35:65) for 15 min. The flow rate was reduced to 2.0 ml./min. and the system equilibrated for 5 min. prior to subsequent injection. A 25 μl aliquot of the eluant in every fifth tube was chromatographed on an analytical system to check for composition prior to combination of the tubes. The analytical system was comprised of a 61 cm. × 2.1 mm. I.D. stainless steel column packed with phenyl/CORASIL (tradename for a bonded phase material for partition chromatography manufactured by Waters Associates, Inc.; consists of a solid glass bead which has been coated with a single layer of silica to which is bonded diphenyldichlorosilane)(37-50 μ particle size). The mobile phase was a 45:55 mixture of acetonitrile:0.01 M sodium acetate pH 4.0 at a flow rate of 0.7 ml./min. Eluant was monitored with a UV detector (LDC) at 254 nm. Tube combinations were made on the basis of the analytical chromatograms. Tubes 61-120 were found to contain the desired musettamycin. These tubes were combined and evaporated in vacuo (45° C.). The dark red residues were flushed repeatedly with methanol and 2 × 100 ml. with methylene chloride. The residue was then triturated with 100 ml. chloroform and filtered to remove inorganic salts. The solid was then evaporated to dryness with dry $N_2$ and dried under high vacuum over $P_2O_5$.

Musettamycin as purified above is characterized by the following data:
Description: dark red crystalline powder
Molecular formula: $C_{36}H_{45}O_{14}N$
Molecular weight: 715.76
Elemental analysis: Theoretical: C, 60.41; H, 6.34; N, 1.95; Experimental: C, 60.27; H, 6.59; N, 1.99; Corrected for .83 $H_2O$ and .83 residue: C, 60.27; H, 6.50; N, 1.99.

Infrared spectrum: The infrared absorption spectrum of musettamycin (KBr pellet) shows major bands at the following wave lengths: 3480, 2970, 2930, 2820, 2770, 1735, 1600, 1450, 1320, 1295, 1220, 1160, 1010 and 990 $cm^{-1}$.

Ultraviolet spectrum: At a concentration of 0.013 g./liter in methanol musettamycin exhibits the following maxima and absorptivities: 233 mμ, 57.7; 256 mμ, 33.2; 284 mμ, 14.5; 466 mμ, 14.3; 490 mμ, 17.4; 510 mμ, 14.6; 524 mμ, 12.9; and 570 mμ, 3.3.

Nuclear magnetic resonance spectra:
a. 100 mHz pmr spectrum: At a concentration of 25 mg./.5 ml. in $CDCl_3$, the spectrum showed the following chemical shifts in ppm and pattern descriptions: 7.66, s; 7.32, s; 7.21, s ($CDCl_3$); 5.50, m; 5.24, m; 5.00, m; 4.48, quartet; 4.10, s; 3.68, s; 4.2 to 3.4, overlapping m's; 2.16, s; 2.5 to 1.3, overlapping m's and 1.3 to 0.9, overlapping doublets and triplets [s=singlet, m=multiplet].

b. 25 mHz cmr spectrum: At a concentration of 200 mg./ml. in $CDCl_3$, the spectrum shows the following observed chemical shifts and intensities (unnumbered peaks are due to solvent):

| No. | Relative Intensity | Freq. in Hz | PPM |
|---|---|---|---|
| 1 | 34 | 4777.66 | 189.816 |
| 2 | 34 | 4654.38 | 184.918 |
| 3 | 60 | 4303.11 | 170.962 |
| 4 | 57 | 4076.06 | 161.941 |
| 5 | 39 | 3980.33 | 158.138 |
| 6 | 45 | 3961.43 | 157.387 |
| 7 | 57 | 3578.36 | 142.168 |
| 8 | 44 | 3327.79 | 132.213 |
| 9 | 52 | 3299.86 | 131.103 |
| 10 | 32 | 3269.30 | 129.889 |
| 11 | 36 | 3258.97 | 129.478 |
| 12 | 32 | 3021.49 | 120.043 |
| 13 | 42 | 2875.63 | 114.249 |
| 14 | 42 | 2816.92 | 111.916 |
| 15 | 37 | 2812.68 | 111.747 |
| 16 | 30 | 2548.48 | 101.251 |
| 17 | 42 | 2489.88 | 98.923 |
|  | 72 | 1967.51 | 78.169 |
|  | 78 | 1935.57 | 76.900 |
|  | 72 | 1903.47 | 75.624 |
| 18 | 27 | 1852.56 | 73.602 |
| 19 | 87 | 1797.79 | 71.426 |
| 20 | 36 | 1791.56 | 71.178 |
| 21 | 34 | 1775.10 | 70.525 |
| 22 | 33 | 1716.43 | 68.193 |
| 23 | 31 | 1670.07 | 66.351 |
| 24 | 30 | 1649.89 | 65.550 |
| 25 | 29 | 1548.63 | 61.527 |
| 26 | 33 | 1431.42 | 56.870 |
| 27 | 64 | 1318.54 | 52.386 |
| 28 | 69 | 1074.95 | 42.708 |
| 29 | 18 | 847.88 | 33.686 |
| 30 | 23 | 819.21 | 32.547 |
| 31 | 29 | 805.76 | 32.013 |
| 32 | 17 | 722.16 | 28.691 |
| 33 | 42 | 449.34 | 17.852 |
| 34 | 56 | 418.12 | 16.612 |
| 35 | 60 | 165.37 | 6.570 |

High pressure liquid chromatogram: The retention time for musettamycin was found to be 11 min. 20 sec. using Waters Associates, Inc. modular components operating at the following parameters: 61 cm. 33 2.1 mm. phenyl/CORASIL support column; 45 to 55 ratio of acetonitrile to .01 M sodium acetate, pH 4; .7 ml./min. flow rate; 254 mμ UV detector.

Melting point: 210°-212° C. Solubility: Soluble in most organic solvents; will crystallize from methanol in higher concentrations at 20° C.; insoluble in water, aliphatic hydrocarbons and ether.

EXAMPLE 11

Purification of marcellomycin

Crude EDTA-washed marcellomycin was subjected to an initial clean-up using a four column bank of μ STYRAGEL (tradename for a gel filtrant column packing material used in gel permeation chromatography; the material consisting of small beads, 8-10 microns in diameter, composed of rigid, crosslinked polymers of styrene divinylbenzene; manufactured by Waters Associates, Inc.) (500-100-100-100 A) with chloroform as a mobile phase. The flow rate for this separation was 0.6-0.7 ml./min. and the elution was monitored with a refractive index detector (Waters Associates, Inc.). Ten runs of 100 gm. each were made and in each case the main peak eluting at 26-32 min. was collected. The main fraction from the 10 runs was combined and evaporated to dryness in vacuo. The dark red amorphous solid was divided into twentyfive, 30-35 mg. fractions. Each was dissolved in 1.0 ml. of a 45:55 acetonitrile: 0.01 M sodium acetate pH 4.0 solvent mixture immediately prior to loading into the chromatographic system consisting of a 1 meter × 4.6 mm. I.D. stainless steel column packed with phenyl/PORASIL B (tradename for a bonded phase material for partition chromatography manufactured by Waters Associates, Inc.; composed of a totally porous silica having liquid phase of diphenyl dichlorosilane chemically bonded to the silica) (37-75 μ particle size). The mobile phase was 45:55 acetonitrile:0.01 M sodium acetate pH 4.0 at a flow rate of 3.0 ml./min. The elution was monitored using a differential refractive index monitor (Waters Associates, Inc.). Fractions were collected at 1.0 min. intervals with the aid of an SMI (Scientific Manufacturing Industries) fraction collector. Fifty-nine tubes were collected and the column was washed at a flow rate of 4.0 ml./min. with acetonitrile and for 15 min. with the mobile phase prior to a subsequent injection. The eluant contained in every fifth tube was chromatographed on an analytical system prior to combination of tubes. The analytical system was composed of a 61 cm. × 2.1 mm. I.D. stainless steel column of phenyl/corasil (tradename for a bonded phase material for partition chromatography manufactured by Waters Associates, Inc.; consists of a solid glass bead which has been coated with a single layer of silica to which is chemically bonded diphenyldichlorosilane) (37–50 μ particle size). The mobile phase consisted of a 45:55 acetonitrile: 0.01 M sodium acetate pH 4.0 solvent mixture with a flow rate of 0.68–0.7 ml./min. The eluant was monitored with a UV detector at 254 nm. Twenty-five μl. of eluant was injected into this system. Tube combinations were made on the basis of the analytical chromatograms. In general, tubes 18–35 were found to contain exclusively the desired marcellomycin component. These tubes were combined and evaporated to dryness in vacuo at 45° C. The residue was flashed repeatedly with methanol and 2 × 100 ml. with methylene chloride. The residue was triturated with 75 ml. of methylene chloride and filtered. The filtrate was evaporated in vacuo (45° C.) to dryness. Dark red residue was then dried under high vacuum over $P_2O_5$.

Marcellomycin as purified above is characterized by the following data:

Description: dark red amorphous powder Molecular formula: $C_{42}H_{55}NO_{17}$; Molecular weight: 845.90; Elemental analysis:

Theoretical: C, 59.64; H, 6.55; N, 1.65; O, 32.15; Experimental: C, 56.32; H, 6.64; N, 1.74; Corrected for $H_2O$ and residue: C, 58.77; H, 6.77; N, 1.82.

Infrared spectrum: The infrared absorption spectrum of marcellomycin (KBr pellet) shows major bands at the following wave lengths: 3450, 2960, 2940, 2820, 2790, 1730, 1615, 1600, 1450, 1260, 1095, 1010 and 800 cm$^{-1}$.

Ultraviolet spectrum: At a concentration of 0.013 g./l. in methanol, marcellomycin exhibits the following maxima and absorptivities: 233 mμ, 47.5; 256 mμ shoulder, 24.7; 284 mμ shoulder, 10.6; 490 mμ, 15.8; 410 mμ shoulder, 3.4; 465 mμ shoulder, 13.2; 480 mμ shoulder, 14.7; 510 mμ shoulder, 12.5; 524 mμ shoulder, 10.6; and 580 mμ shoulder, 1.1.

Nuclear magnetic resonance spectra:

a. 100 mHz pmr spectrum: At a concentration of 25 mg./5 ml. in $CD_2Cl_2$, the spectrum showed the following chemical shifts in ppm and pattern descriptions: 7.63, s; 7.24, s; 5.52, m; 5.30, m; 5.33, m ($CD_2Cl_2$); 4.94, m; 4.50, quartet; 4.30 to 3.90, overlapping m's; 3.69, s; 2.70 to 0.09, overlapping m's; and 2.19, s [s=singlet, m=multiplet].

b. 25 mHz cmr spectrum: At a concentration of 60 mg/2 ml. of $CD_2Cl_2$, the spectrum shows the following observed chemical shifts and intensities (unnumbered peaks are due to solvent):

| No. | Relative Intensity | Freq. in Hz | PPM |
|---|---|---|---|
| 1 | 38 | 3454.09 | 137.574 |
| 2 | 31 | 3331.45 | 132.727 |
| 3 | 56 | 2964.01 | 118.088 |
| 4 | 37 | 2739.81 | 109.156 |
| 5 | 49 | 2642.13 | 105.264 |
| 6 | 37 | 2627.41 | 104.678 |
| 7 | 52 | 2246.11 | 89.487 |
| 8 | 30 | 1995.14 | 79.488 |
| 9 | 46 | 1969.58 | 78.469 |
| 10 | 38 | 1926.64 | 76.759 |
| 11 | 35 | 1918.43 | 76.432 |
| 12 | 37 | 1682.08 | 67.015 |
| 13 | 26 | 1543.35 | 61.488 |
| 14 | 32 | 1489.08 | 59.326 |
| 15 | 29 | 1484.44 | 59.141 |
| 16 | 45 | 1213.98 | 48.366 |
| 17 | 51 | 1195.68 | 47.636 |
| 18 | 55 | 1155.94 | 46.053 |
| 19 | 50 | 768.18 | 30.605 |
| 20 | 54 | 516.93 | 20.595 |
| 21 | 91 | 455.17 | 18.134 |
| 22 | 64 | 444.15 | 17.695 |
| 23 | 43 | 433.12 | 17.256 |
| 24 | 49 | 378.19 | 15.067 |
| 25 | 54 | 348.77 | 13.895 |
| 26 | 50 | 339.07 | 13.509 |
| 27 | 57 | 305.61 | 12.176 |
| 28 | 63 | 303.14 | 12.077 |
| 29 | 49 | 206.56 | 8.229 |
| 30 | 53 | 96.91 | 3.861 |
|  | 67 | 54.60 | 2.175 |
|  | 136 | 27.27 | 1.087 |
|  | 175 | 0.01 | 0.000 |
|  | 165 | −27.03 | −1.077 |
|  | 67 | −54.44 | −2.169 |
| 31 | 103 | −264.55 | −10.540 |
| 32 | 40 | −478.75 | −19.074 |
| 33 | 38 | −491.67 | −19.589 |
| 34 | 50 | −514.78 | −20.509 |
| 35 | 47 | −533.08 | −21.238 |
| 36 | 32 | −610.57 | −24.326 |
| 37 | 49 | −899.27 | −35.828 |
| 38 | 67 | −918.94 | −36.611 |
| 39 | 80 | −926.83 | −36.926 |
| 40 | 79 | −1202.93 | −47.926 |

High pressure liquid chromatogram: The retention time for marcellomycin was found to be 10 min. 24 sec. using Waters Associates, Inc. modular components operating at the following parameters: 61 cm. × 2.1 mm. phenyl/CORASIL support column, 45 to 55 ratio of acetonitrile to .01 M sodium acetate, pH 4; .68 to 7 ml./min. flow rate; 254 mμ UV detector.

Melting Point: Softening at 134–135° C.; gradual thickening, but does not melt up to 300° C.

We claim:

1. A process for producing musettamycin which comprises cultivating Actinosporangium sp. A.T.C.C. 31127 in an aqueous nutrient medium containing assimilable sources of nitrogen and carbon under submerged aerobic conditions until a substantial amount of musettamycin is produced by said organism in said culture medium.

2. A process for producing marcellomycin which comprises cultivating Actinosporangium sp. A.T.C.C. 31127 in an aqueous nutrient medium containing assimilable sources of nitrogen and carbon under submerged aerobic conditions until a substantial amount of marcellomycin is produced by said organism in said culture medium.

* * * * *